United States Patent
Gorritxategi et al.

(10) Patent No.: US 9,341,612 B2
(45) Date of Patent: May 17, 2016

(54) SYSTEM AND METHOD FOR MONITORING A FLUID

(71) Applicant: ATTEN2 Advanced Monitoring Technologies, S.L.U., Eibar (Guipúzcoa) (ES)

(72) Inventors: Eneko Gorritxategi, Eibar (ES); Jon Mabe, Eibar (ES)

(73) Assignee: ATTEN2 ADVANCED MONITORING TECHNOLOGIES S.L.U., Elgoibar (Guipuzcoa) (ES)

( * ) Notice: Subject to any disclaimer, the term of this patent is extended or adjusted under 35 U.S.C. 154(b) by 0 days.

(21) Appl. No.: 14/778,009

(22) PCT Filed: Mar. 27, 2013

(86) PCT No.: PCT/ES2013/070207
§ 371 (c)(1),
(2) Date: Sep. 17, 2015

(87) PCT Pub. No.: WO2014/154915
PCT Pub. Date: Oct. 2, 2014

(65) Prior Publication Data
US 2016/0069856 A1   Mar. 10, 2016

(51) Int. Cl.
*G01N 33/28* (2006.01)
*G01N 21/85* (2006.01)
*G01N 21/25* (2006.01)

(52) U.S. Cl.
CPC ............ *G01N 33/2888* (2013.01); *G01N 21/25* (2013.01); *G01N 21/85* (2013.01)

(58) Field of Classification Search
CPC ...................... G02B 27/017; G02B 2027/0178; G02B 2027/014; G02B 27/0093; G02B 2027/0187; G02B 26/08; G02B 26/0833; G02B 26/085; G02B 26/0875; G02B 26/10; G02B 26/101; G02B 27/2214; G02B 27/225
See application file for complete search history.

(56) References Cited

U.S. PATENT DOCUMENTS

| 7,920,260 B2 * | 4/2011 | Mantele ............. G01N 15/0205 356/336 |
| 2008/0024761 A1 | 1/2008 | Kong et al. |
| 2015/0369722 A1 * | 12/2015 | Donner ............. G01N 15/1459 73/864.72 |

FOREIGN PATENT DOCUMENTS

| CN | 102818756 | 12/2012 |
| WO | WO 97/40360 | 10/1997 |
| WO | WO 01/55768 | 8/2001 |

OTHER PUBLICATIONS

PCT International Search Report, PCT/ES2013/070207, completion date: Jan. 27, 2014; 7pages.

*Primary Examiner* — Michael P Stafira

(57) ABSTRACT

System (18, 28) for inspecting oil, which comprises a cell (280) through which oil (281) flows through a pipe. Inside said cell (280) the system comprises a lighting system (284) based on at least one LED diode and configured to supply a beam of white light to the flow of oil (281); a diffuser (286) situated between the lighting system (284) and the flow of oil (281), configured to provide homogeneous lighting to the lit area; an image capture system (282, 382) situated on the opposite side of the pipe through which the oil (281) flows in respect of the lighting system (284) and configured to capture a sequence of images of the oil which flows inside said pipe; a lens (283) situated between the image capture system (282) and the flow of oil (281), configured to focus the captured images; a calibration device (287) situated between the lens (283) and the flow of oil (281); a processor (2851) configured to process said sequence of images and to determine the presence of particles and bubbles and a degradation value of the oil.

11 Claims, 3 Drawing Sheets

SYSTEM AND METHOD FOR MONITORING A FLUID

TECHNICAL FIELD

The present invention relates to the field of fluid monitoring for determining the general condition of fluids from the point of view of their degradation and also particle content. More specifically, it relates to the field of oil monitoring, in particular lubricating oils, in order to obtain through said monitoring their state of degradation, and also to obtain information on the machinery lubricated by said oils on the basis of their particle content.

BACKGROUND OF THE INVENTION

Industrial machinery, whether engines or power generating turbines, compressors, multipliers, etc. undergo unforeseen shutdowns and failures, often associated to aspects related to lubrication. The reduction in the service life of this industrial machinery often gives rise to unnecessary maintenance costs. Current 'off-line' measurement methodologies (oil sample analysis in the laboratory) do not provide a sufficiently early detection of the degradation process due to the low frequency with which these measurements are usually taken. Furthermore, in many contexts (transport, industrial, power . . . ) this control methodology entails a significant logistical and financial burden. To deal with this drawback, the idea is to develop a new generation of sensors capable of analysing the machine's condition in real time.

Critical machinery could benefit from an increase in reliability, reduction in maintenance costs and early problem identification through the use of smart sensors.

Lubricating oil is one of the key components in some of these machines and provides a lot of information regarding the machine's condition. Oil heating, for example, can be a sign that the machine is not operating in optimum conditions, and the presence of particles in the oil may indicate a future failure or considerable wear in the lubricated components. It could even point to the existence of cracks or faults in joints that could allow the entry of external contaminants.

Some of the parameters that it could be interesting to monitor in lubricating oil are as follows: particle determination (for example, quantification, classification of size or determination of shape), bubble content in the system or oil degradation based on colour. Below is a brief description of these parameters.

Particle determination in lubricated systems is a key aspect in many sectors and applications, since the particles provide information on the condition of the machine that is being monitored. In other words, the detection of particles in the oil is indicative in many cases of a situation that will generate a future failure or a breakdown in the machine, or the presence of a fault in filters or joints.

At present, most of these lubricated systems install filtering solutions that remove the particles from the lubrication system. However, filtering systems do not act on the root cause of the problem, and instead are limited to reducing the consequences of particle generation, whose presence in the lubrication system could accentuate the generation of more serious problems. At the same time, filtering systems present a series of limitations: they can become clogged or saturated, not being capable of removing any more particles.

Traditionally, laboratory techniques have been used in order to determine the quantity and type of wear particles present in lubricating oil, and also to classify them according to size. Subsequently, different technologies for on-line particle detection have started to emerge, such as:

Detectors through light blockage: These systems are based on the reduction in intensity that the detectors receive when a particle passes through the measuring cell to which a beam of light is supplied. No image is collected, instead this reduction in light is observed, principally on some wavelength. It is not possible to determine the shape of the particles but it is possible to determine their size. The main problem with these systems is the presence of water or air bubbles, which are counted as particles.

Detectors through pore blockage: They also use optical detection, but without image gathering. However, before this, the oil is made to pass through a mesh (10 micras approx.) for classification avoiding the presence of water and air bubbles at the time that the measurement is taken.

Magnetic/electric detectors: Sensors that use a magnetic principle to detect ferromagnetic particles on the fluid, by making the fluid pass through a magnetic field that is altered by the presence of the ferromagnetic particles.

Detectors through image analysis: These analyse an image, quantifying particle content according to size, shape and type, using a neural network algorithm. One would cite, for example, analysis equipment that uses an image capture system, together with a laser lighting system and powerful image processing software installed on a computer. It is also capable of identifying contaminants, free water, and fibres. The equipment quantifies wear particles having a size between 4-100 micras, and the shape of particles larger than 20 micras. Particle analysis in this range is useful for detecting mechanical faults in a wide variety of lubricated systems. Depending on the shape, the particle is classified as: a) cutting; b) fatigue; c) sliding; d) non-metallic.

Below is a mention of patents that disclose image-analysis detectors:

For example, U.S. Pat. No. 5,572,320 describes an image analysis detector that includes a lighting system based on a pulsed laser. Detection is carried out by means of a planar array of light sensitive photodiodes or phototransistors. However, the system of U.S. Pat. No. 5,572,320 is not capable of discriminating between particle shapes. Also, the measuring cell of U.S. Pat. No. 5,572,320 consists of a moving part that positions the oil in a specific place, and this complicates development and can be an important source of errors.

Meanwhile, U.S. Pat. No. 7,385,694B2 describes a detector through image analysis that includes a lighting system based on a pulsed laser and a camera for gathering images of the oil subjected to such lighting. However, the device of this patent does not allow a homogenous lighting to be provided over an inspection area that is greater than the beam of light itself. Also, the device requires a pump in order to pump the fluid to the measuring zone.

Another of the parameters that it could be interesting to monitor in lubricating oil is the bubble content in the system, since this can be indicative of foam generation in the oil and air retention in the system, which is undesirable. Both must be controlled and reduced to a maximum in order to achieve optimum functioning of the oil inside the system. This is critical in systems such as the multipliers of wind turbines. The maximum acceptable foam levels for used oil, according to method ASTM-D892, must not exceed:

| Temperature | Formation (5'blowing) | Stability (10'blowing) |
|---|---|---|
| 24° C. | 100 | 10 |
| 93.5° C. | 200 | 20 |
| 24° C. | 100 | 10 |

The content in retained oil must not exceed 25% in respect of new oil according to ASTM-D3427.

Finally, oil degradation based on colour is another parameter that may be interesting to monitor in lubricating oil:

Oil degradation is a key indicator of oil quality and how it fulfils its lubricating mission. It does not provide information on the machine directly, but indirectly from the speed of degradation it would be possible to extract information regarding the machine's operation. The degradation process of oil follows several very well-known steps: first it suffers a loss in additive content, then acidic compounds are generated, and finally, when it is in an advanced state of degradation, polymerisation processes begin in these acidic compounds that have been generated. The percentage of acidic constituents (in the form of additives in the case of new lubricating oils and in the form of oxidation compounds in the case of lubricating oils in service) is determined through analytical techniques.

DESCRIPTION OF THE INVENTION

The present invention attempts to resolve the drawbacks mentioned above by means of a system for inspecting oil, which comprises a cell through which oil flows along a pipe. The system comprises inside said cell: a lighting system based on at least one LED diode and configured to supply a beam of white light to the flow of oil; a diffuser situated between the lighting system and the flow of oil, configured to provide homogeneous lighting in the lit area; an image capture system situated on the opposite side of the pipe through which the oil flows in respect of the lighting system and configured to capture a sequence of images of the oil that flows inside said pipe; a lens situated between the image capture system and the oil flow, configured to focus the captured images; a calibration device situated between the lens and the oil flow; a processor configured to process said sequence of images and to determine the presence of particles and a value for the oil degradation.

Preferably, the lighting system comprises a polarisation control system of at least one LED diode configured to avoid emission fluctuations due to changes in temperature.

Preferably, the diffuser is situated closing and sealing a hole made in the pipe through which the fluid flows.

In a possible embodiment, the diffuser is a frosted glass.

Preferably, the image capture system is a camera.

In a possible embodiment, the calibration device situated between the lens and the oil flow comprises a plurality of markings designed to calibrate the system. Preferably, the calibration device is situated closing and sealing a hole made in the pipe through which the oil flows.

In another aspect of the present invention, a method is provided for auto-calibration of the system for inspecting oil mentioned above, which comprises the stages of:
carrying out on the calibration device at least one marking of known dimensions;
capturing an image of an oil using the image acquisition system;
adjusting the capture parameters to increase the contrast of the captured image until finding the system's optimum polarisation;
capturing a new image;
binarising said image with dynamic threshold;
in said image, identifying the geometry of said at least one marking;
carrying out the horizontal and vertical measurement of the number of pixels and applying a correction in respect of their real sizes;
saving said correction as the calibration measurement for the absolute dimensional measurements obtained by the system during its subsequent use.

In another aspect of the present invention, a method is provided for the detection and discrimination of particles and bubbles in an oil by means of the system for inspecting an oil described above, which comprises the stages of:
capturing an image of the oil using the image acquisition system;
adjusting the capture parameters to increase the contrast of the captured image until finding the system's optimum polarisation;
capturing a new image;
binarising said image with dynamic threshold;
conditioning the binary image;
detecting the objects that are considered bubbles or particles by means of applying techniques for searching for connected components or for detection and dimensional identification of pixel groupings;
in order to distinguish between bubble and particle:
applying an inversion of the binary image in those regions where potential particles or bubbles have been detected;
applying dilation-based conditioning to those inverted regions of interest;
applying to those zones techniques for detecting connected components in order to detect holes in the original groupings of pixels, identifying as bubbles those zones that present pixel groupings with holes, and identifying as particles those pixel groupings detected without an inner hole;
based on the pixel groupings, counting and calculating the size of the bubbles and particles, wherein the calculation of said size comprises applying to those pixels the dimensional correction obtained in the auto-calibration method described above.

In another aspect of the present invention, a method is provided for obtaining an oil degradation parameter using the system for inspecting an oil described above, which comprises the stages of:
applying to the lighting system described above, a temperature compensation algorithm;
capturing an image of the oil with the three colour channels—red, green, blue—using the system's image acquisition system;
extracting from said image the regions with pixel groupings and generating an image with those zones marked with a negative value;
carrying out a measurement of the transmittance in the red band $I_R$, transmittance in the blue band $I_B$ and transmittance in the green band $I_G$, adding up the value of each one of the pixels divided by the number of pixels used for the inspection;
applying an algorithm to obtain a degradation parameter n the basis of said three colour channels.

Preferably, said obtaining of a degradation parameter based on said three colour channels is obtained from the formula $CI=1*I_R+0.5*I_G+0.5*I_B$, wherein CI is the value of the oil's colour index.

BRIEF DESCRIPTION OF THE DRAWINGS

As a complement to the description and with a view to contributing towards an improved understanding of the characteristics of the invention, according to an example of a practical example thereof, a set of drawings is attached as an integral part of this description, which by way of illustration and not limitation, represent the following.

DESCRIPTION OF AN EMBODIMENT OF THE INVENTION

Figure 1:
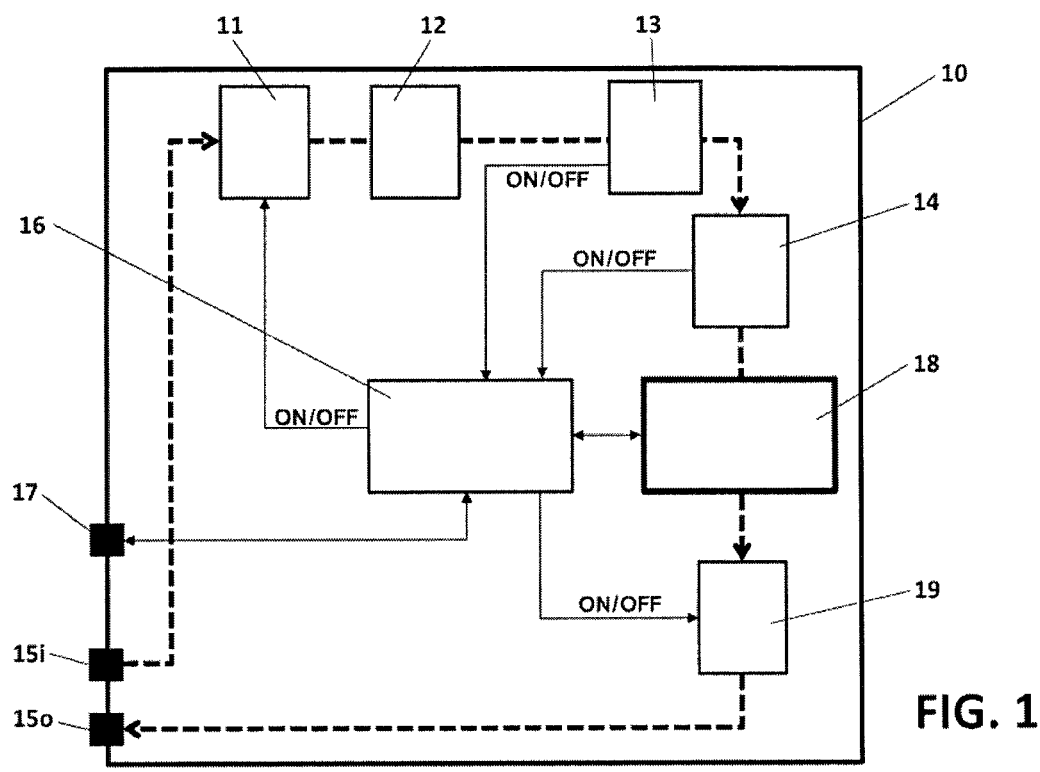
FIG. 1 represents a general outline of the monitoring system of the invention.

FIG. 1 represents a general outline of the monitoring or inspection system of the invention. The system is composed of a series of sub-systems connected to each other and contained within a receptacle or container 10. The sub-systems are as follows:

A hydraulic conditioning sub-system, made up of components for flow control 12, oil flow control by means of electrovalves 11 19, pressure control 13, safety filter 14 and the inlet 15i and outlet 15o piping. The reading and operation of the active hydraulic elements is carried out from the electronic sub-system 16. It is noteworthy that the hydraulic conditioning sub-system does not include any pump, unlike the system described in U.S. Pat. No. 7,385,694B2. In a preferred embodiment, the system of the invention is designed to be installed in a by-pass of the lubricating system of certain machinery. The installation takes advantage of the pressure differences for the fluid to circulate to the measurement module 18 where the oil inspection will take place.

An electronic sub-system formed by an embedded electronic platform 16 for managing all active sub-systems and managing data channels. This embedded electronic platform 16 performs the global management of information and control of the hydraulic and measurement sub-systems. This sub-system is considered to include the internal and external connection technologies and the power system 17.

A sensor sub-system or measurement sub-system 18, which represents the sub-system where the measurement is carried out and which is described below. The measurement module 18 delivers totally valid measurement values without the need for processing.

The container and fastening system 10 which incorporates the external hydraulic and electrical connections and the fastening system (not shown in FIG. 1) to the installation's place of destination. The system 10 is specifically designed for its direct integration into the lubricating systems of machinery but without affecting the operating conditions thereof. This is achieved by means of the hydraulic sub-systems of the sensor which make it possible to carry out controlled sampling with low content in lubricating oil. The container and the fastening system 10 houses and integrates the different elements in an appropriate manner and allows external communication for the intake and output of the fluid, through the respective inlet 15i and outlet 15o (as the measurement is carried out in the measurement sub-system 18) and provides the communication interfaces and power supply 17 in order to be able to carry the sensor's results to the machine in question or wherever required.

The hydraulic sub-systems in turn allow the fluid to be measured to be conditioned, thereby reducing the effects of external conditions or factors on the end result. The system has also been developed to avoid the influence of environmental factors such as changes in temperature. In this sense, the sensor system has temperature measurers that actuate the intensity of the light emitting diode and thereby prevent differences in emission related to changes in temperature.

As can be seen from FIG. 1, the fluid enters the container 10 through the inlet 15i. The flow of fluid follows the direction of the dotted arrow line. The fluid circulates through the inside of the container 10 through appropriate channelling means, such as pipes. Through the inlet and outlet fittings and the sub-systems it is possible to carry out a representative sampling of the fluid (for example, oil) and to condition it to obtain representative measurements of its real condition.

Flow control 12 makes it possible for the system to obtain a fixed flow which makes it possible to know the amount of fluid that is being measured and thereby to obtain the particle concentration therein. In other words, the flow control 12 makes it possible to give values of, for example 100 particles per milliliter. Otherwise, it would only be possible to say that 100 particles were detected, in absolute terms.

Optionally there may be a safety filter or filter with pressure control 14 which serves to prevent large-sized particles from entering the measurement module 18, which could damage or soil the module's windows and even ensure that the system does not become clogged with large particles.

The pressure switch 13 is a pressure system that ensures that there is pressure in the system and therefore guarantees that there is a flow of the fluid (for example, of oil). Therefore, it is a pressure switch designed to identify low pressures. The issue is that the machines in which the sensor is installed (module 18) are not functioning continuously, and when they are stopped there is no oil pressure, meaning that there is no entry of oil in the sensor, which results in the measurement eventually taken not being representative, because oil is not being measured. With the pressure switch 13 there is detection of pressure when there is and when there isn't pressure, in order to validate a taken measurement and thereby ensure that it is oil and not air that is being measured.

Both the inlet electrovalve 11 and the outlet electrovalve 19 perform the function of allowing the oil in or not. When the electrovalve is "ON", the system is open for the oil to pass; and when the electrovalve is "OFF", the system is closed and the oil does not enter. This is carried out so that the oil is not continuously flowing through the system, for two important reasons: (1) to carry out controlled sampling and interfere as little as possible with the machine's lubricating systems; (2) to ensure that the hydraulic sub-systems are not affected by dirt that could be generated by the continuous flow of oil.

The ON/OFF arrows indicate in respect of the components next to which they appear in FIG. 1, that these components are controlled electronically. Specifically, on electrovalves 11 19 the ON/OFF arrows indicate the opening and closing off of entry to the oil; and in the pressure switch 13 and filter 14 the ON/OFF arrows provide an indication of the pressure level in the system. The pressure switch 13 is "ON" when a specific pressure value is exceeded and then it is assumed that oil has entered; in filter 14, the pressure control that it incorporates ensures that the oil does not exceed a maximum pressure value.

Figure 2:
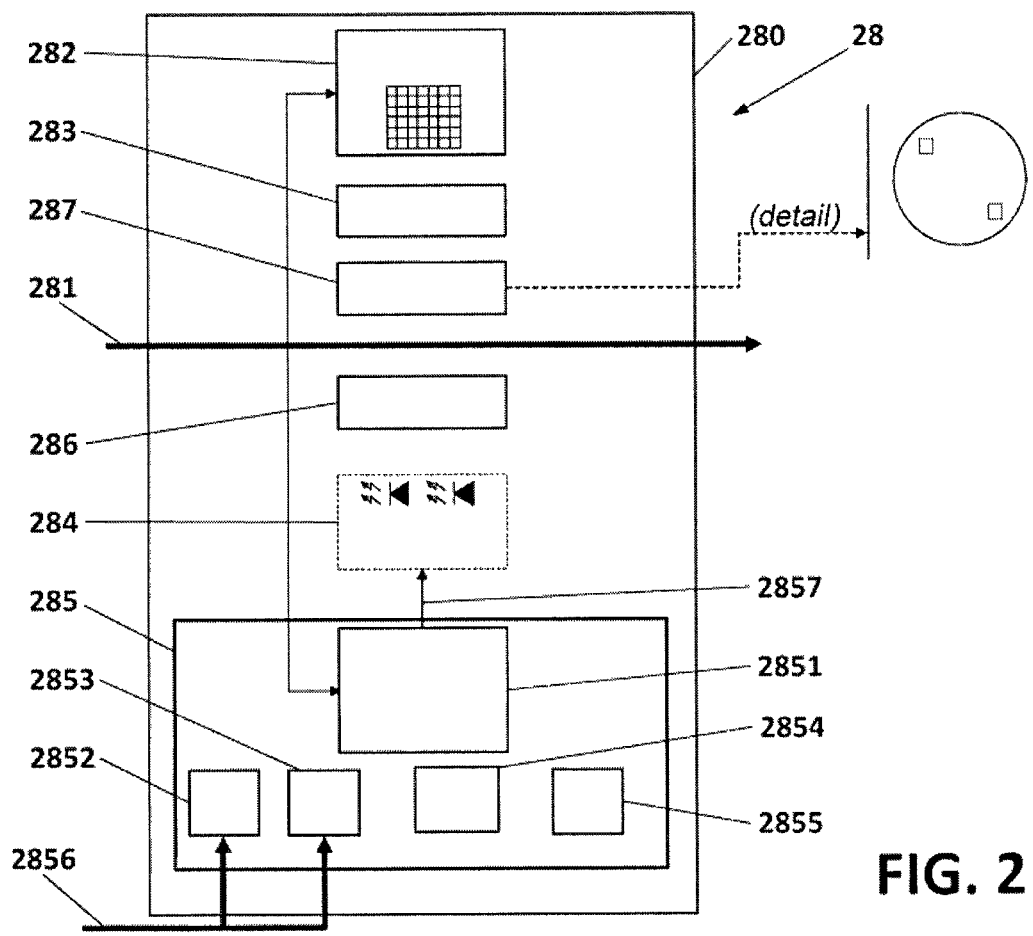
FIG. 2 shows an outline of the measurement module according to a possible embodiment of the invention.

FIG. 2 represents an outline of the measurement sub-system or sensor sub-system of the invention (sub-system 18 in FIG. 1). This module or measurement sub-system 28 has been conceived as an autonomous sub-system with totally independent functioning, which delivers auto interpretable measurements, calibrated and corrected for the entire defined operating range. As described below, the measurement sub-system 28 operates on a micromechanical cell 280 through which the fluid 281 under supervision circulates. In a preferred embodiment, this fluid is oil, more preferably lubricating oil. The fluid 281 is driven inside channelling means, such as for example a pipe.

The measurement sub-system or module 28 comprises an optical part and an electronic part (or video acquisition and processing sub-system). As can be seen, this video acquisition and processing sub-system is an independent electronic from the embedded electronic platform 16 of the complete system. The first is found inside the measure module 18 28, whereas the second is a module 16 extraneous to the measurement module. This video acquisition and processing sub-system carries out the activities related to measurements, among other things. The video acquisition and processing sub-system is made up of an embedded image capture system 282 and by electronics 285 which comprise an embedded processor 2851. The measurement sub-system 28 is based on an embedded artificial vision measurement system, wherein by means of an image capture system 282 a video sequence is captured which is processed in an embedded processor 2851. The objective of the processing is to determine the presence of particles and/or bubbles and the degradation value of the fluid (for example, oil) (OD). The arrow between the image capture system 282 and the embedded processor 2851 outlines the video data and control lines.

In a possible embodiment, an acquisition and processing system of 4 frames per second (4FPS) is used. For example, and Omnivision detector can be used with a 14 megapixel camera.

The optical part comprises a lighting system 284 to subject the flow of fluid 281 to a beam of light and an image capture system 282 to capture a video sequence that will afterwards be processed in an embedded processor 2851 of the electronics part 285. In a preferred embodiment, the embedded processor 2851 is a DSP device (Digital Signal Processor).

The lighting system 284 is designed to supply a beam of white light to the fluid. Preferably, the lighting system is based on one or more LED diodes which continuously light the flow 281 which circulates through the micromechanical cell 280. In other words, preferably, the lighting system is a LED emitter 284. Preferably, the emission system 284 has a control system (closed loop control) of the polarisation of the LED emitter based on changes in temperature which prevent fluctuations in emission due to said changes in temperature. As a person skilled in the art knows, when the temperature rises there is a reduction in the emission of the LEDs due to a decrease in the efficiency of the photons. By means of this control, if the temperature rises the power is increased so that the apparent emitted light remains constant. In a possible embodiment, the lighting system 284 comprises also a photodiode near the lighting zone to calculate the error of that closed loop. The embedded processor 2851 controls the lighting system 284, through LED control signals and compensation data 2857.

Between the lighting system 284 (preferably LED emitter) and the flow of fluid 281 (which circulates inside a pipe), a diffuser 286 is placed having the principal mission of diffusing the amount of light emitted by the lighting system 284 in order to obtain a homogenous lighting over the entire area (amount of fluid, preferably oil) that is being inspected. In a preferred embodiment, the diffuser 286 is a window. The diffuser 286 is called a "window" because it is the element that provides visual access to the fluid under inspection. Thanks to this diffuser 286 it is possible to light the area under inspection in a homogeneous manner.

The diffuser (diffuser window) 286 is placed closing a hole made in the pipe through which the fluid 281 flows. In other words, the fluid (oil) passes through the pipe or conduit, but transversally to the direction of the fluid a hole is made through which the fluid will be inspected and measured. The hole is preferably circular and the diffuser window 286 is also preferably. This diffuser 286 prevents the fluid (oil) leaking through the holes made. This window 286 acts as a seal so that the fluid does not leak through the transversal hole. The diffuser 286 is moreover made of a transparent material that allows light through it. Therefore, the lighting system 284 can light the fluid appropriately, and by means of the detection system 282 it is possible to visualise this zone and to capture the image of the fluid. In a preferred embodiment, the window 286 is a glass, for example a frosted glass.

The light that is not absorbed by the fluid is gathered by means of a detector (for example, a photodiode or photodiode array). In an inspection system by means of artificial vision, by using back lighting, the optical receiver element (the 2D photodiode array) collects the light that passes through the flow of fluid (for example, oil).

Opposite the lighting system 284 (LED emitter), on the other side of the pipe through which the flow 281 circulates, an image capture system 282 is situated to capture the video sequence (which is no more than a train of images) of the zone of interest in the passage of the fluid (preferably oil). This image capture is carried out with a defined spatial resolution and maintaining the general criteria of reduced size and low cost. In other words, the "defined spatial resolution" refers to the fact that the capture system 282 is capable of determining a defined minimum size of particle, which is in the region of 4 micras over an inspection area of about 100 $mm^2$. This resolution is achieved by optimising several conditions, such as the area to be inspected, the size of the camera, its number of pixels, and the characteristics of the lens 283 (which is mentioned below). The module 28 and in general the complete system 10 must have a small size and be as compact as possible.

In a preferred embodiment, the image capture system 282 is a camera, more preferably a camera based on CMOS sensor or CMOS detector (the CMOS sensor is the camera component that receives the image). Therefore, a CMOS camera has a 2D array of photoreceptors manufactured with CMOS technology. For this reason, occasionally in this text the expression "CMOS sensor" or "CMOS detector" is used to refer to the camera 282. The images captured by this camera are processed in the embedded processor 2851 of the electronics part 285. In a preferred embodiment, the embedded processor 2851 is a DSP device (Digital Signal Processor). This embedded processor 2851 is the one that analyses for each image whether there are bubbles and particles and counts them following the procedure described further below. In other words, the processor is responsible for extracting the image from the CMOS and processing it. To do this, it has an intermediate memory 2854 for subsequent processing. In a possible embodiment, this intermediate memory is a DDR2 external memory.

Between the image capture system (CMOS detector) 282 and the flow of fluid 281 under inspection there is a lens 283, preferably a macro lens, responsible for transporting the image from the object to the camera 282, in other words, it is responsible for the camera 282 appropriately focusing what is required to be detected. The lens allows objects to be focused in the light-reactive element and objects to be captured. The lens carries the light in focus to the light receiving area.

Between the lens (macro lens) 283 and the pipe that collects the flow of fluid 281 under inspection another optical device or optical window 287 is placed which is also placed sealing a hole made in the pipe through which the fluid 281 flows. This hole is opposite the hole described above (and covered by the diffuser 286). This second optical window 287 also acts as a seal so that the fluid does not leak through the transversal hole. It is also made of a transparent material that allows light to pass through it. The hole is preferably circular and the optical window 287 is also preferably. Preferably, the window 287 is a calibration window which comprises markings or patterns that allow it to be auto-calibrated (as explained below). The markings are of a specific size and in this way it is possible to automatically calibrate the equipment avoiding errors or dispersions due to assembly or manufacture. FIG. 2 illustrates an enlarged close-up of the optical device or optical window 287 which includes two markings by way of an example.

The minimum size of particle that it must be possible to discriminate is of approximately 4 μm. The area to be captured in each image by the image capture system (CMOS detector) 282 must be such that it is capable of capturing particles of 4 μm and more. In a preferred embodiment, the area to be captured is of several square millimeters. In one example, said area to be captured is of 100 mm². At the same time, the distance between the object (plane of passage of the fluid under inspection) and the CMOS detector 282 is desirably as minimum as possible and does not exceed approximately 100 mm, so that the system can be as compact and small as possible. The maximum depth of field (range in which the lens 283 is capable of providing a focused image) is marked by the width of the passage of the oil through the micromechanical cell 280.

As has been explained, the measurement sub-system or module 28 comprises diffuser means 286 of the inspected area. Thanks to the LED diodes and to these diffuser means, it is possible to obtain a homogeneous lighting of all of the inspected area. Conventional oil supervision systems do not homogenise the area under supervision, meaning that particle detection is not optimal. The inventors have observed that, especially when white light is used, this homogenisation is important in order to obtain reliable results.

The video acquisition and processing sub-system (embedded image capturer 282 and electronics 285 with embedded processor 2851) is the one responsible for acquiring and processing the video sequence supplied by the camera 282 of the optical sub-system. The power and precision of the measurement or sensor sub-system 28 is the direct result of the processing algorithms run by this video acquisition and processing sub-system.

In FIG. 2, the electronic part 285 comprises, in addition to the embedded processor 2851, auxiliary systems (communication interface 2852, power source 2853, memory 2854, temperature sensor 2855 . . . ). Reference 2856 indicates the electronic interface of communication and the power source). Also, there is a software part, formed by the group of algorithms in charge of the detection and classification of particles, bubble detection and determination of degradation.

Figure 3:
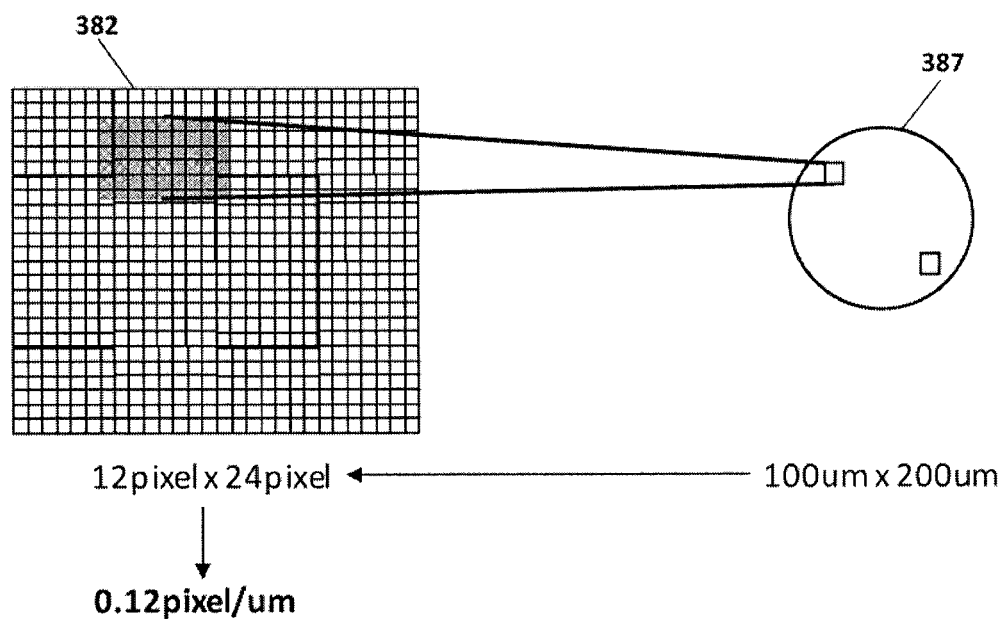
FIG. 3 illustrates schematically a method for auto-calibration of the measurement system, according to a possible embodiment of the invention.

In a particular embodiment, the video acquisition and processing sub-system is responsible for applying algorithms for the dimensional calibration of the measurement module 28. Basically, the auto-calibration is based on identifying using the image capture system (CMOS detector) 282 markings, of a known size, made on the calibration window 287 so that any identified image can then be scaled. One example of these markings is shown in the close-up of the calibration window 287 of FIG. 2. Although this is explained in detail further below, FIG. 3 illustrates schematically the auto-calibration of the proposed measurement system. The calculation of the size of the detected particles is the product of the entire configuration of the optical sub-system. It is known that the manufacturing and assembly tolerances introduce a dispersion in the system's focus, and consequently in the apparent size of the objects captured on the camera. In order to correct this deviation, compensation is applied through dimensional auto-calibration of the module. This auto-calibration is the result of applying some algorithms of dimensional identification (which are explained further below) to known shapes marked in the calibration window 287 and then applying said proportionality to all of the dimensions calculated by the system.

The inventors have observed that this auto-calibration makes it possible to diminish the effects of the mechanical and assembly tolerance on the size of the images of particles captured on the camera. The auto-calibration allows, in contrast to conventional oil supervision systems, automatic compensation of these differences in the sizes of the objects captured due to the manufacturing and assembly dispersion. It also means that it is not necessary to dimensionally calibrate each unit of equipment. Also, it makes the system more robust against potential degradations occurring in the machine. In other words, the auto-calibration system and algorithm impose the required precision of the system (4 μm) on the auto-calibration markings and not on the entire micromechanical system, although in practice the result is equivalent to imposing said precision requirements on the whole system.

What follows is a description of the different algorithms and procedures of the invention, for the detection and classification of particles, fluid (oil) degradation, and others:
Detection, Discrimination and Classification of Particles and Bubbles Algorithm (DDC-PB)

The particle detection and discrimination algorithm must one the one hand discriminate between bubble and particle, and count and classify particles by size. Optionally, it comprises also algorithms for control of lighting/exposure to improve detection sensitivity. The particle detection and discrimination algorithm comprises the following steps:

a. Capturing an image with the image acquisition system 282 382. Preferably, this image is taken at the system's medium resolution and in gray scale.

b. Adjusting the capture parameters, preferably by means of applying control of the exposure time of the image acquisition system 282 382 and current control of the LED 2857 in order to increase the contrast of the captured image until finding the system's optimum polarisation.

c. After adjusting the capture parameters, capturing a new image, preferably with maximum resolution in gray scale.

d. Binarising the image with dynamic threshold (based preferably on analysis of the mean and standard deviation of luminance in different zones of the image).

e. Conditioning the binary image, preferably by means of the 2D enlargement technique, which makes it possible to group dispersed pixels together and to generate denser pixel concentrations.

f. Applying techniques for searching for connected components or dimensional detection and identification of pixel groupings. This technique is used to detect objects that are considered to be bubbles or particles. From this point onwards, methods of discrimination between bubble and particle are applied.

g. Applying an inversion of the binary image in those regions where objects have been detected (potential particles or bubbles).

h. Applying a conditioning based on enlargement to those inverted regions of interest.

i. Applying in those zones the same techniques of connected component detection. In this case, holes in the original pixel groupings are being detected.
j. Those zones that present pixel groupings with holes are identified as bubbles due to the fact that the proposed lighting system makes the bubbles be captured as circular objects having a very shiny zone within their circumference due to the light diffraction occurring in the air contained by the bubble.
k. Consequently, those pixel groupings detected as not having a hole inside are considered to be particles.
l. Next, the bubbles and particles are counted and classified. Size classification is carried out preferably in number of pixels of the highest value between the height and the width of the pixel grouping.
m. To conclude, with regard to calculating the real size of the particles and delivering a normalised value based on standard classifications, applying to those sizes in pixels the dimensional correction provided by the dimensional auto-calibration algorithm (see the following point).

Dimensional Auto-Calibration (ACD)

The calculation of the size of the particles is the product of the entire configuration of the optical sub-system. It is known that the manufacturing and assembly tolerances introduce a dispersion in the system's focus, and consequently in the apparent size of the objects captured on the image capture system. In order to correct this deviation, in a particular embodiment, compensation is applied through dimensional auto-calibration of the measurement module 28. Basically, the auto-calibration is based on identifying by means of the image capture system 282 markings, of a known size, made on the optical device 287 so that it is then possible to scale (apply that proportionality to) any identified image.

The auto-calibration algorithm presents the following stages:

a. Capturing an image using the image acquisition system 282 382. Preferably, this image is taken at medium resolution and in gray scale.
b. Adjusting the capture parameters, preferably by means of applying control of the exposure time of the image acquisition system 282 382 and current control of the LED 2857 in order to increase the contrast of the captured image until finding the system's optimum polarisation.
c. After adjusting the capture parameters, capturing a new image preferably with maximum resolution in gray scale.
d. Binarising the image with dynamic threshold (based preferably on the analysis of the mean and standard deviation of luminance in different zones of the image).
e. Identifying the geometry of each pattern shape, by means of applying classification techniques to the areas found (the markings of known size made on window 287) taking into account the size and characteristics of the shape, such as length, circularity, compactness, roundness, rectangularity, or others.
f. After identifying the geometries of the pattern shapes, carrying out the horizontal and vertical measurement of the number of pixels and applying a correction in respect of their real sizes in micrometers.
g. Using this correction as a calibration measurement of all absolute dimensional measurements supplied by the system during its subsequent use.

FIG. 3 shows an example of execution of stage f above: The image acquisition system 382 captures one of the markings or patterns of the optical device 387. Given that this marking has been made intentionally on the optical device 387, it is known that its real dimensions are, for example, 100 µm×200 µm. At the same time, the capture made by the image acquisition system 382 provides a size of the captured object of, for example 12 pixels×24 pixels. After applying the processing and the corresponding algorithm, it is established that the correction factor to be applied is 0.12 pixel per µm.

Oil Degradation Parameter Calculation Algorithm (OD)

In order to calculate the fluid (preferably oil) degradation parameter there is a discrimination made to segment the image and use only those areas that are "clean" of particles and bubbles. In those segments, colorimetry algorithms are applied. Due to the fact that this is an analysis of colour intensity, in this case, a known lighting/exposure configuration must be used, corrected only to offset the effect of the temperature.

The algorithm for calculating the degradation parameter presents the following stages:

a. Applying a compensation algorithm for the temperature of the lighting system.
b. Capturing an image preferably at medium resolution with the three colour channels (RGB).
c. Applying an algorithm of detection and discrimination of particles and bubbles (DDC-PB) and extracting the regions with pixel groupings to generate an image having those zones marked with a negative value (nonexistent).
d. Carrying out a mean of the intensity of each one of the channels or bands $I_R$ $I_B$ $I_G$ (red band transmittance, blue band transmittance, and green band transmittance, respectively), adding up the value of each one of the pixels divided by the number of pixels used for the inspection.
e. Applying an algorithm to obtain a degradation parameter based on the three colour channels RGB. In a preferred embodiment, applying the following formula: $CI=1*I_R+0.5*I_G+0.5*I_B$, wherein CI is the value of the fluid's colour index.

Not all processing must be performed in the same cycle, meaning that response time requirements are relaxed.

Throughout this document, the word "comprises" and variants thereof (such as "comprising", etc.) must not be interpreted as having an exclusive meaning, in other words, they do not exclude the possibility of what is being described incorporating other elements, steps, etc.

At the same time, the invention is not limited to the specific embodiments described herein and also extends, for example, to variants that may be embodied by an average person skilled in the art (for example, with regard to the choice of materials, dimensions, components, configuration, etc.), within the scope of what is inferred from the claims.

The invention claimed is:

1. A system (18, 28) for inspecting oil, which comprises a cell (280) through which oil (281) flows through a pipe, the system (18, 28) being characterised in that it comprises inside said cell (280):

a lighting system (284) based on at least one LED diode and configured to supply a beam of white light to the flow of oil (281);
a diffuser (286) situated between the lighting system (284) and the flow of oil (281), configured to provide homogeneous lighting to the lit area;
an image capture system (282, 382) situated on the opposite side of the pipe through which the oil (281) flows in respect of the lighting system (284) and configured to capture a sequence of images of the oil that flows inside said pipe;

a lens (283) situated between the image capture system (282) and the flow of oil (281), configured to focus the captured images;

a calibration device (287) situated between the lens (283) and the flow of oil (281); and a processor (2851) configured to process said sequence of images and to determine the presence of particles and bubbles and a degradation value of the oil.

2. The system (18, 28) of claim 1, wherein said lighting system (284) comprises a system for controlling the polarisation of at least one LED diode configured to prevent emission fluctuations due to changes in temperature.

3. The system (18, 28) for claim 1, wherein said diffuser (286) is situated closing off and sealing a hole made in the pipe through which the fluid (281) flows.

4. The system (18, 28) of claim 3, wherein said diffuser (286) is a frosted glass.

5. The system (18, 28) of claim 1, wherein said image capture system (282, 382) is a camera.

6. The system (18, 28) of claim 1, wherein said calibration device (287) situated between the lens (283) and the flow of oil (281) comprises a plurality of markings designed to calibrate the system.

7. The system (18, 28) of claim 6, wherein said calibration device (287) is situated for closing off and sealing a hole made in the pipe through which the oil (281) flows.

8. A method for auto-calibration of the system (18, 28) for inspecting oil according to claim 1, which comprises the steps of:

making on the calibration device (287) at least one marking of known dimensions;

capturing an image of an oil using the image acquisition system (282, 382);

adjusting the capture parameters to increase the contrast of the captured image until finding the system's optimum polarisation;

capturing a new image;

binarising said image with dynamic threshold;

in said image, identifying the geometry of said at least one marking;

taking the horizontal and vertical measurement in the number of pixels and applying a corrector in respect of their real sizes; and saving that correction as a calibration measurement for the absolute dimensional measurements obtained by the system (18, 28) during its subsequent use.

9. A method for detecting and discriminating particles and bubbles in oil by means of the system (18, 28) for inspecting oil according to claim 1, which comprises the steps of:

capturing an image of an oil using the image acquisition system (282, 382);

adjusting the capture parameters to increase the contrast of the captured image until finding the system's optimum polarisation;

capturing a new image;

binarising said image with dynamic threshold;

conditioning the binary image;

detecting the objects that are considered bubbles or particles by applying techniques for the search of connected components or for dimensional detection and identification of pixel groupings;

in order to discriminate between bubble and particle:

applying an inversion of the binary image in those regions where potential particles or bubbles have been detected;

applying a conditioning based on enlargement of those inverted regions of interest;

applying in those zones techniques for the detection of connected components in order to detect holes in the original pixel groupings, identifying as bubbles those zones that present pixel groupings with holes, and identifying as particles those pixel groupings not having a hole inside them; and based on the pixel groupings, counting and calculating the size of the bubbles and particles, wherein the calculation of said size comprises applying to those pixels the dimensional correction obtained using the auto-calibration method of claim 8.

10. A method for obtaining an oil degradation parameter using the system (18, 28) for inspecting oil of claim 1, which comprises the steps of:

applying to the lighting system (284) of the system (18, 28) of claim 1, a temperature compensation algorithm;

capturing an image of the oil with the three colour channels—red, green, blue—using the image acquisition system (282, 382) of the system (18, 28);

extracting from said image the regions with pixel groupings and generating an image with those zones marked with a negative value;

taking a mean of transmittance in the red band IR, transmittance in the blue band IB and transmittance in the green band IG, adding up the value of each one of the pixels divided by the number of pixels used for the inspection; and applying an algorithm to obtain a degradation parameter based on said three colour channels.

11. The method of claim 10, wherein obtaining a degradation parameter based on said three colour channels is obtained on the basis of the formula $CI=1*I_R+0.5*I_G+0.5*I_B$, wherein CI is the value of the oil's colour index.

* * * * *